United States Patent [19]
Thiel et al.

[11] Patent Number: 5,646,331
[45] Date of Patent: Jul. 8, 1997

[54] PROCESS FOR WORKING UP RESIDUES FROM THE RAW ESTER DISTILLATION IN THE PREPARATION OF DIMETHYL TEREPHTHALATE(DMT)

[75] Inventors: Ralf Thiel, Niederkassel; Reinhard Auschner, Troisdorf, both of Germany

[73] Assignee: Huels Aktiengesellschaft, Marl, Germany

[21] Appl. No.: 695,777

[22] Filed: Aug. 12, 1996

[30] Foreign Application Priority Data

Aug. 23, 1995 [DE] Germany ............ 195 30 970.7

[51] Int. Cl.⁶ .................................................. C07C 69/82
[52] U.S. Cl. ........................... 560/78; 560/98; 560/99
[58] Field of Search ............................ 560/78, 98, 99

[56] References Cited

U.S. PATENT DOCUMENTS

| | | | |
|---|---|---|---|
| 4,126,755 | 11/1978 | Bunger et al. | 560/77 |
| 5,286,896 | 2/1994 | Korte et al. | 560/77 |
| 5,338,882 | 8/1994 | Korte et al. | 562/483 |

FOREIGN PATENT DOCUMENTS

| | | |
|---|---|---|
| 0 053 241 | 6/1982 | European Pat. Off. . |
| 0 464 046 | 1/1992 | European Pat. Off. . |
| 11 42 858 | 1/1963 | Germany . |
| 2 010 137 | 9/1971 | Germany . |
| 22 44 662 | 4/1974 | Germany . |
| 40 26 733 | 2/1992 | Germany . |
| WO90/09367 | 8/1990 | WIPO . |

*Primary Examiner*—Samuel Barts
*Attorney, Agent, or Firm*—Oblon, Spivak, McClelland, Maier & Neustadt, P.C.

[57] ABSTRACT

A process for working up, by methanolysis, a residue fraction resulting from raw ester distillation in a DMT process is provided, the process involving:

admixing the residue fraction with liquid or gaseous methanol, or both to give a reaction mixture;

providing the reaction mixture to a reactor, wherein, prior to entry into the reactor, the reaction mixture is at a temperature of from 230° to 265° C.; and methanolysing the reaction mixture in the reactor, wherein a bottom portion of the reactor is maintained at a temperature of from 230° to 265° C.

20 Claims, 1 Drawing Sheet

PROCESS FOR WORKING UP RESIDUES FROM THE RAW ESTER DISTILLATION IN THE PREPARATION OF DIMETHYL TEREPHTHALATE(DMT)

BACKGROUND OF THE INVENTION

1. Field of the Invention

The present invention relates to a process for working up a residue fraction by methanolysis, the residue fraction originating from the raw ester distillation of the DMT production process.

2. Discussion of the Background

Dimethyl terephthalate (DMT) is produced on a large scale in numerous plants around the world. DMT is an important starting compound for the preparation of polyesters. Polyesters have long been used in the preparation of fibers, films, including photographic films, magnetic tapes or bottles of polyethylene terephthalate, to name only a few.

The conventional Witten DMT process essentially comprises (cf. EP-B 0 464 046, DE-A 40 26 733) the process steps of (1) Oxidation of para-xylene (p-X) and methyl para-toluate (p-TE) with downstream waste gas purification;

(2) Esterification of the reaction products from the oxidation with methanol;

(3) Separation of the raw ester formed into a) a fraction which is recirculated to the oxidation, b) a raw DMT fraction containing more than 99% by weight of DMT and c) a high-boiling residue fraction including its work-up; and (4) Purification of the raw DMT fraction, for example by washing, recrystallization or pure distillation.

It is also possible to prepare terephthalic acid from DMT-rich fractions by targeted hydrolysis.

The oxidation of a mixture of para-xylene (p-X) and methyl para-toluate (p-TE or pT ester) is generally carried out in the liquid phase using atmospheric oxygen in the presence of a heavy metal catalyst (DE-C 20 10 137) at a temperature of from about 140° to 180° C. and a pressure of from about 4 to 8 bar abs. The oxidation step results in a reaction mixture which contains predominantly monomethyl terephthalate (MMT), p-toluic acid (p-TA) and terephthalic acid (TA) dissolved or suspended in p-TE. This mixture is esterified with methanol at a temperature of from about 250° to 280° C. at a pressure of from 20 to 25 bar abs. The raw ester obtained is separated by distillation into a p-TE fraction, a raw DMT fraction and a high-boiling, catalytic-containing residue fraction. The p-TE fraction is recirculated to the oxidation and the raw DMT fraction is converted via subsequent purification steps into the desired product quality.

The residue fraction originating from the raw distillation is generally further treated by methanolysis. FIG. 1 shows the flow diagram of a conventional single-stage methanolysis. In the reaction distillation column (1.1), the residues (1.2) and superheated methanol vapour (1.3) are continuously introduced in countercurrent at atmospheric pressure. The bottom of the column is additionally heated by means of a heat-transfer oil (1.4). The methanolysis is carried out at a temperature of from 265° to 280° C. Part of the residues are converted into materials which can be reused in the process. Acids present in the residue fraction are esterified in the methanolysis, part of the high-boiling organic compounds are dissociated and organic products of value already present are separated from undesired organic compounds which can no longer be used. The valuable or useful materials thus obtained go together with excess methanol via the top of the column to the dephlegmator (1.5) and are subsequently recirculated to the process, i.e. to the oxidation (1.6). The bottom residue formed in the methanolysis is generally conveyed to catalyst recovery (1.7). It is found in practice that carbon deposits and blockages occur in the reaction column during methanolysis, resulting in more frequent and unplanned stoppages of the unit.

EP-B 0 464 046 discloses a two-stage methanolysis for working up the residue from the raw ester distillation. The first methanolysis stage essentially comprises a reactor with upstream heat exchanger and circulation system, with a distillation column arranged downstream of the top of the reactor. In contrast to the first stage, the second methanolysis stage comprises a reaction distillation column. In both stages, additional methanol in vapour form is fed into the respective residue circuit upstream of the heat exchangers, i.e. before entry into the respective methanolysis reactors. The operating temperatures for both methanolysis stages are more than 265° C.; particularly in the second methanolysis stage. Furthermore, each methanolysis stage is operated as a circuit and only partial streams are replaced, with the throughput amounts of the residue fraction to be worked up naturally being comparatively small. In addition, the two-stage methanolysis requires a high investment and high maintenance cost for operation of the plant.

SUMMARY OF THE INVENTION

Accordingly, one object of the present invention is to provide a process which makes it possible to work up the residue fraction formed in the raw ester distillation during DMT production in a very economical manner.

A further object of the present invention is to provide a process for working up the residue fraction from raw ester distillation in the DMT process by methanolysis which reduces carbon deposits in the reactors and pipe systems of the methanolysis.

These and other objects of the present invention have been satisfied by the discovery that carbon deposits can be substantially reduced in a methanolysis procedure wherein liquid and/or gaseous methanol are added to the raw ester distillate, the temperature of the mixture before entry into the methanolysis reactor is maintained at from 230° to 265° C. and the temperature in the bottom of the reactor is controlled to be from 230° to 265° C., and wherein, in the present process, the reactor bottoms are preferably not subjected to a throughput-reducing circulation procedure, by means of which the capacity of the methanolysis stage is able to be significantly increased.

BRIEF DESCRIPTION OF THE FIGURES

A more complete appreciation of the invention and many of the attendant advantages thereof will be readily obtained as the same becomes better understood by reference to the following detailed description when considered in connection with the accompanying Figures, wherein.

DETAILED DISCUSSION OF THE PREFERRED EMBODIMENTS

The present invention relates to a process for working up a residue fraction resulting from raw ester distillation in a DMT process, comprising:

admixing the residue fraction with liquid or gaseous methanol, or both to give a reaction mixture;

providing the reaction mixture to a reactor, wherein, prior to entry into the reactor, the reaction mixture is at a temperature of from 230° to 265° C.; and methanolysing the reaction mixture in the reactor, wherein a bottom portion of the reactor is maintained at a temperature of from 230° to 265° C.

In the present process liquid and/or gaseous methanol is preferably fed into the residue fraction. Before entry into the methanolysis reactor, the mixture has a temperature of from 230° to 265° C., preferably from 245° to 255° C. The temperature in the bottom of the reactor is maintained at from 230° to 265° C., preferably from 245° to 255° C. The methanolysis is preferably carried out at a pressure of from 1 to 40 bar abs., more preferably at a pressure of from 1 to 3 bar abs.

Figure 2:
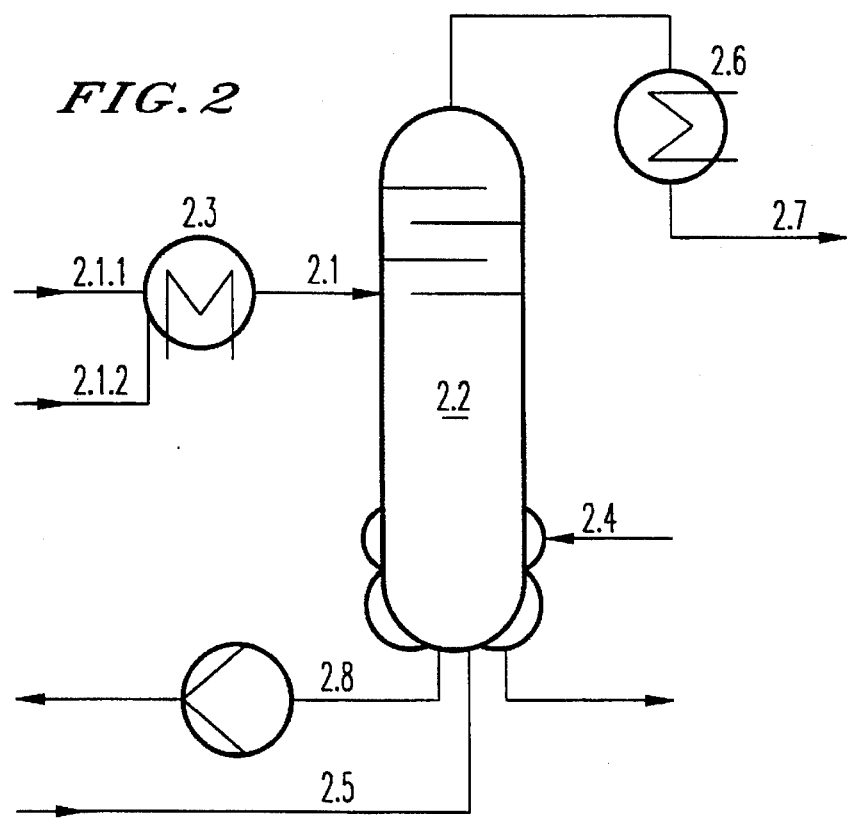
FIG. 2 shows a flow diagram of a preferred embodiment of the methanolysis procedure of the present invention.

FIG. 2 shows a flow diagram of a preferred embodiment of the process of the invention, where the methanolysis is carried out, in particular, in a single stage and the residue fraction from the raw ester distillation (2.1.1) is preferably worked up in a reaction distillation column (2.2). Preferably, the residue fraction admixed with methanol (2.1.2) is passed through a heat exchanger (2.3) before entry into the methanolysis reactor, in order to provide the mixture of residue fraction and methanol (2.1.2) to the reaction distillation column (2.2) at the required temperature. The heat exchanger can be any conventional heat exchanger and is preferably operated electrically, by means of high-pressure steam, by means of a preheated heat-transfer oil, for example MARLOTHERMR, or a combination thereof. In the process of the invention, the bottom of the reactor (2.4) can also be heated using any conventional heating means. The bottom of the reactor (2.4) is preferably heated electrically, by means of high-pressure steam, by means of a preheated heat-transfer oil or a combination thereof. As described above, the residue fraction pretreated with methanol is preferably reacted in the methanolysis reactor with further addition of methanol (2.5). Here too, the methanol can be fed in liquid and/or vapour form.

In the process of the present invention, the reaction is carried out under particularly gentle and comparatively mild conditions relative to conventional methanolysis procedures. The useful products obtainable in the reaction are preferably recirculated via a dephlegmator (2.6) to the DMT process, i.e. to the oxidation stage (2.7). In the process of the present invention, the proportion of useful product in the bottom of the reaction column can be reduced to about 3.5% compared with about 8.5% in conventional processes. In the present process, part of the reactor bottoms can be bled off and fed to a process for catalyst recovery (2.8) if desired. The fill level in the bottom of the reactor should preferably be kept essentially constant. The fill level can, for example, also be regulated by means of the amount of feed of the residue from the raw ester distillation. Portions can be taken from the bottom of the reactor continuously or discontinuously. Catalyst recovery is carried out, for example, by extraction (cf. EP-B 0 053 241).

By means of the gentle procedure in the process of the present invention, it is possible to increase the reaction time of the methanolysis reaction, which represents a further economic advantage. Particularly surprising is the fact that the process of the present invention enables the yield over the entire DMT process to be increased by about 0.5%, even without circulation of the reactor bottoms. This is a significant commercial improvement in the economics of the process.

Figure 1:
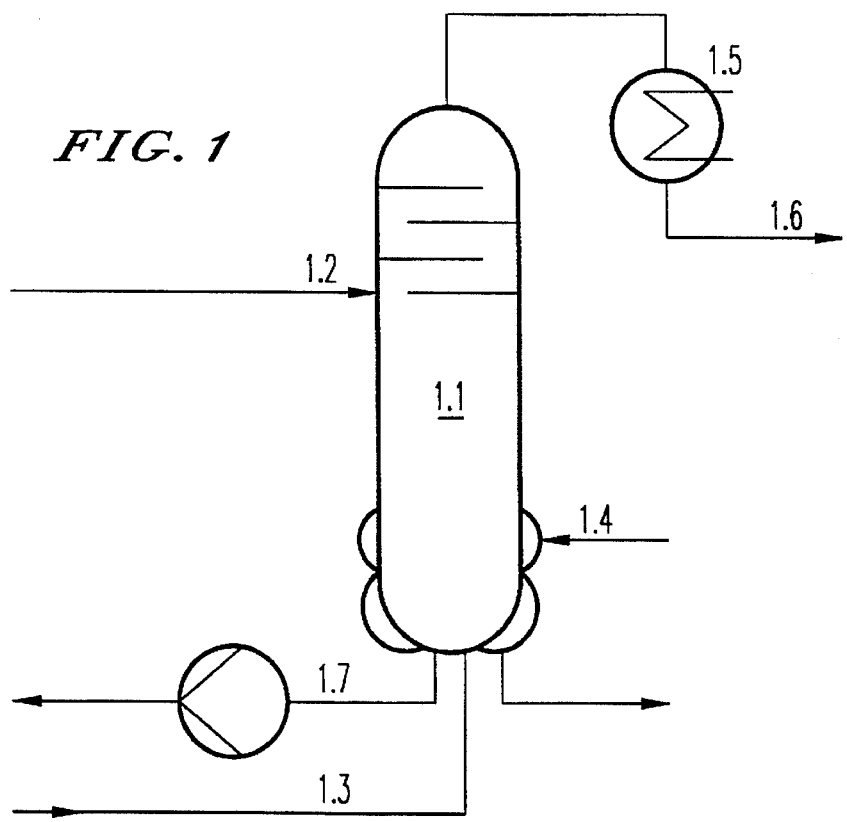
FIG. 1 shows a flow diagram of a conventional single-stage methanolysis procedure.

Legends for FIG. 1

Flow diagram of a conventional single-stage methanolysis reactor for working up a residue from the raw ester distillation in the preparation of DMT 1.1 Reaction distillation column
1.2 Feed of the residue from the raw ester distillation
1.3 Gaseous methanol feed
1.4 Heating of the bottom of the reaction column
1.5 Dephlegmator
1.6 Recirculation of the useful product to the process
1.7 Substream of the bottom residue to catalyst recovery Legends for FIG. 2

Flow diagram of a single stage methanolysis reactor of the present invention for working up a residue from the raw ester distillation in the preparation of DMT 2.1 Feed of the residue (2.1.1) from the raw ester distillation, to which methanol (2.1.2) has been added
2.2 Reaction distillation column
2.3 Heat exchanger
2.4 Heating of the bottom of the reaction column
2.5 Methanol feed
2.6 Dephlegmator
2.7 Recirculation of the useful products to the process
2.8 Substream of the bottom residue to catalyst recovery This application is based on German Patent Application 195 30 970.7, filed with the German Patent Office on Aug. 23, 1995, the entire contents of which are hereby incorporated by reference.

Obviously, additional modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for working up a residue fraction resulting from raw ester distillation in a DMT process, comprising:
   admixing the residue fraction with liquid or gaseous methanol, or both to give a reaction mixture;
   providing the reaction mixture to a reactor, wherein, prior to entry into the reactor, the reaction mixture is at a temperature of from 230° to 265° C.; and
   methanolysing the reaction mixture in the reactor, wherein a bottom portion of the reactor is maintained at a temperature of from 230° to 265° C.

2. The process according to claim 1, wherein, prior to entry into the reactor, the reaction mixture is at a temperature of from 245° to 255° C.

3. The process according to claim 1, wherein the bottom portion of the reactor is maintained at a temperature of from 245° to 255° C.

4. The process according to claim 1, wherein the methanolysing step is carried out at a pressure of from 1 to 40 bar abs.

5. The process according to claim 4, wherein the methanolysing step is carried out at a pressure of from 1 to 3 bar abs.

6. The process according to claim 1, wherein the reaction mixture of the residue fraction admixed with methanol is brought to the required temperature using a heat exchanger prior to entry into the reactor.

7. The process according to claim 6, wherein the heat exchanger is operated by a means selected from the group consisting of electricity, high-pressure steam, preheated heat-transfer oil and combinations thereof.

8. The process according to claim 1, wherein the bottom portion of the reactor is heated by a means selected from the group consisting of electricity, high-pressure steam, pre-heated heat-transfer oil and combinations thereof.

9. The process according to claim 1, wherein during the methanolysing step, additional methanol is added to the reactor.

10. The process according to claim 9, wherein the additional methanol is added as liquid methanol.

11. The process according to claim 9, wherein the additional methanol is added as gaseous methanol.

12. The process according to claim 1, wherein the reactor is a reaction distillation column.

13. The process according to claim 1, wherein the methanolysing step results in production of reactor bottoms, which are not subjected to circulation.

14. The process according to claim 1, wherein the methanolysing step results in production of reactor bottoms, wherein a portion of the reactor bottoms is bled off and subjected to a catalyst recovery step.

15. The process according to claim 1, wherein said methanolysing step is a single stage methanolysis.

16. The process according to claim 1, wherein products from the methanolysing step are recirculated to the DMT process.

17. The process of claim 16, wherein the products from the methanolysing step are passed through a dephlegmator prior to recirculation to the DMT process.

18. The process of claim 1, wherein, prior to entry into the reactor, the reaction mixture is at a temperature of from 245° to 255° C., wherein the bottom portion of the reactor is maintained at a temperature of from 245° to 255° C., and wherein the methanolysing step is carried out at a pressure of from 1 to 40 bar abs.

19. The process of claim 18, wherein the methanolysing step is carried out at a pressure of from 1 to 40 bar abs.

20. The process of claim 1, wherein fill level of the reaction mixture in the reactor is maintained at an essentially constant level.

* * * * *